United States Patent [19]

Mielenz et al.

[11] Patent Number: 4,493,893
[45] Date of Patent: Jan. 15, 1985

[54] PROCESS FOR CLONING THE GENE CODING FOR A THERMOSTABLE ALPHA-AMYLASE INTO *ESCHERICHIA COLI* AND *BACILLUS SUBTILIS*

[75] Inventors: Jonathan R. Mielenz; Susan Mickel, both of LaGrange Park, Ill.

[73] Assignee: CPC International Inc., Englewood Cliffs, N.J.

[21] Appl. No.: 472,646

[22] Filed: Mar. 11, 1983

Related U.S. Application Data

[63] Continuation of Ser. No. 225,287, Jan. 15, 1981, abandoned.

[51] Int. Cl.$^3$ .................... C12N 15/00; C12N 1/00; C12N 9/26; C12P 21/00
[52] U.S. Cl. ................. 435/172.3; 435/68; 435/317; 435/201; 935/14; 935/29; 935/56; 935/60; 935/72; 935/73; 935/74
[58] Field of Search ............... 435/68, 201, 172, 317; 935/14, 29, 56, 60, 72, 73, 74

[56] References Cited

U.S. PATENT DOCUMENTS 4,237,224  12/1980  Cohen et al. ............... 435/172

FOREIGN PATENT DOCUMENTS 0034470  8/1981  European Pat. Off. .

OTHER PUBLICATIONS

Perlman, Advances in Applied Microbiology, vol. 24, 1978, Academic Press, N.Y., pp. 257-259.
Yoneda et al., Cloning of a Foreign Gene Coding for Alph Amylase in *Bacillus subtilis*, *Biochem and Biophysical Research Com.*, vol. 91, 1979, pp. 1556-1564.
Sidler et al., The Production of Extracellular Thermostable Neutral Proteinase and Alph-Amylase by *Bacillus stearothermophilus*, *European Journal of Applied Microbiology*, 1977, vol. 4, pp. 255-266.
Calewell, D. B., Journal of Bacteriology, 110, 667-676, (1972).
Cohen et al., Proc. Nat. Acad. Scil., U.S.A., 69, 2110-2114, (1972).
Berns, et al., Journal Molecular Biology, 11, 476-490, (1965).
Clewell, et al., Biochemistry, 9, 4428-4440, (1970).
Smith et al., J. Biol. Chem., 179, 53, (1949).
Chung et al., Biochem. J. 185, 387-395, (1980).
Radloff, et al., Proc. Natl. Acad. Sci., U.S.A., 57, 1514, 1521, (1967).
Goebel et al., Molec. Gen. Genet., 157, 119-129, (1977).
El-Gewely et al., Anal. Biochem., 102, 423-428, (1980).
Chang et al., Molec. Gen. Genet., 168, 111-115, (1979).
Shinomiya et al., Isolation of a *Bacillus subtilis* Transformant Producing Thermostable α-amylase by DNA from a Thermophilic Bacterium, *Biochemical and Biophysical Res. Com.*, 1980, vol. 96, pp. 175-179.
Shinomiya, et al., Cloning of Thermostable α-amylase Gene Using *Bacillus subtilis*, Phage pH or a Vector *Agri. Biol. Chem.*, vol. 45, 1981, pp. 1733-1735.
MacDonald, et al., "Structure of a Family of Rat Amylase Genes", Nature, vol. 287, pp. 117-122, Sep. 11, 1980.
Bingham, et al., "Characterization of *Bacillus stearothermophilus* Plasmid pAB124 and Construction of Deletion Variants", *J. Gen. Microbiol.*, 119, 109-115, (1980).

*Primary Examiner*—Esther M. Kepplinger
*Assistant Examiner*—K. S. McCowin
*Attorney, Agent, or Firm*—Stanley M. Parmerter

[57] ABSTRACT

An improved process for producing a thermostable alpha-amylase enzyme is described. The gene coding for the alpha-amylase is incorporated into a chimeric plasmid which is produced in multiple copies by a host microorganism.

22 Claims, No Drawings

4,493,893

PROCESS FOR CLONING THE GENE CODING FOR A THERMOSTABLE ALPHA-AMYLASE INTO ESCHERICHIA COLI AND BACILLUS SUBTILIS

This application is a continuation of application Ser. No. 225,287 filed Jan. 15, 1981, now abandoned.

FIELD OF THE INVENTION

This invention relates to chimeric plasmids which contain a gene coding for a thermostable alpha-amylase enzyme and to a process for their production. Cloning the gene into *Escherichia coli* or *Bacillus subtilis* and use of the resulting microorganisms for production of a thermostable alpha-amylase enzyme are also described.

BACKGROUND OF THE INVENTION

Large quantities of glucose-containing syrups are manufactured by the enzymatic hydrolysis of corn starch. The first step of this process is usually accomplished by treating a starch-water mixture with an alpha-amylase enzyme at temperatures near the boiling point of water. A thermostable alpha-amylase is most efficient at these temperatures. For this reason, there is a great incentive to obtain a low-cost source of such a thermostable enzyme.

The alpha-amylases used commercially are produced by various microorganisms. It is known that these microorganisms contain genetic material which codes for the production of the enzymes by the organism. This genetic material is present in the form of deoxyribonucleic acid, hereafter referred to as DNA, within the cell.

Most genetic material in a bacterium exists as giant DNA molecules which are present as the chromosome of the cell. However, a certain amount of the genetic material may also be present in the form of smaller closed circular molecules of DNA, known as plasmids.

By techniques referred to as genetic engineering, it is possible to transfer a portion of the DNA from one organism to another. Various workers have attempted to use these techniques to develop microorganisms which are superior alpha-amylase producers.

One technique that has been used is to remove the total DNA, i.e., chromosomal plus plasmid DNA, from a microorganism known to produce an amylase. Fragments of this DNA are then linked with the DNA of a bacteriophage. The bacteriophage containing this combined DNA is used to infect another microorganism whereby it transfers this genetic material onto the chromosomal DNA of the microorganism. The cells of the infected organism that receive DNA containing an amylase gene in an active form become amylase producers. These cells can be selected and grown for further use.

An additional genetic engineering technique that has been used with thermostable alpha-amylases involves extracting the total DNA from a microorganism known to produce such amylases. Some fragments of the DNA are transformed into a new host microorganism whereby they are incorporated into the chromosome of the host microorganism. Any cells into which the DNA containing active amylase-coding genetic material has been introduced are then selected and grown.

It has now been found that DNA coding for a thermostable alpha-amylase can exist in a naturally-occurring plasmid. Furthermore, it has been found that such naturally-occurring genetic material containing a thermostable alpha-amylase coding gene can be combined directly with another plasmid, known as a plasmid vector, to give a synthetic plasmid, hereafter called a chimeric plasmid. This chimeric plasmid can be inserted into and multiplied in a new host microorganism. This permits the development of microorganisms that are superior alpha-amylase producers which can be grown readily on a commercial scale. It is to the use of the newly-discovered, naturally-occurring plasmids containing alpha-amylase genes, the formation of chimeric plasmids containing their genetic material, and the development of new microorganisms containing these chimeric plasmids, that the present invention is directed.

SUMMARY OF THE INVENTION

In accordance with the present invention, there is provided a process for preparation of a chimeric plasmid which contains a gene coding for a thermostable alpha-amylase. This is accomplished by first cutting naturally-occurring plasmid DNA that contains a gene coding for the thermostable alpha-amylase to obtain a linear DNA sequence containing the alpha-amylase coding gene. A vector is also cut to obtain a second linear DNA sequence. Finally, the two linear DNA sequences are joined forming the chimeric plasmid.

Also disclosed is the chimeric plasmid obtained using as a donor a naturally-occurring plasmid containing a gene coding for a thermostable alpha-amylase. The chimeric plasmid is prepared by cutting DNA from the donor and combining the resulting DNA fragments with a vector which has been similarly cut.

Finally, in accordance with the present invention, there is provided a process for preparing a thermostable alpha-amylase in high yields. At least one chimeric plasmid containing the alpha-amylase gene is introduced into a host microorganism. The microorganism containing the chimeric plasmid is cultured in a suitable medium. Then the alpha-amylase produced by the cultured microorganism is isolated.

This invention provides a process for producing multiple copies in a single cell of the gene coding for a thermostable alpha-amylase. It also provides a means for tranferring the amylase gene into microorganisms that can be grown more easily than the donor microorganism. Thus, increased yields of the enzyme are readily obtained.

DETAILED DESCRIPTION OF THE INVENTION

For the purpose of this specification, the following definitions are provided for the various terms used herein:

1. Naturally-Occurring Plasmid: The term "naturally-occurring plasmid" as employed in this application, is used to refer to any plasmid DNA which is present in a microorganism found in nature.
2. Chimeric Plasmid: The term "chimeric plasmid" is used as employed generally in the art to refer to a plasmid of recombinant DNA formed from a donor microorganism and suitable vector plasmid by some technique of genetic engineering.
3. Thermostable alpha-Amylase: The term "thermostable alpha-amylase" as employed in this application, refers to any alpha-amylase preparation capable of retaining at least about 60% of its initial activity when held at 90° C. and at a pH of 6.0 for 45 minutes in the presence of calcium ion.

4. alpha-Amylase Gene: A segment of DNA which codes for the alpha-amylase produced within the cell and includes necessary regulatory information for the synthesis of a catalytically-active alpha-amylase.

The chimeric plasmids of this invention are prepared using DNA from a naturally-occurring donor microorganism which contains a gene coding for a thermostable alpha-amylase enzyme. Suitable donor microorganisms are found in the thermophilic bacteria classified as *Bacillus stearothermophilus* (abbreviated *B. stearothermophilus*) and *Thermus flavus* (abbreviated *T. flavus*). Strains of *Bacillus licheniformis* (abbreviated *B. licheniformis*) are also suitable donor microorganisms. Strains of *B. stearothermophilus* particularly suitable for the use as a source of donor DNA are those strains selected from the group consisting of *B. stearothermophilus*, ATCC Nos. 31,195; 31,196; 31,197; 31,198; 31,199 and 31,783, variants and mutants thereof and submutants of said mutants.

It has been discovered that plasmids having a gene coding for a thermostable alpha-amylase enzyme are present in a number of these microorganisms. Plasmid DNA is particularly suitable as a source of the donor DNA, since it can be purified easily by means of an ultracentrifuge. This gives a DNA source for the process in which the amylase genes are highly concentrated and free from much extraneous and undesirable genetic material.

Any vector that is compatible with the host microorganism can be used to form the chimeric plasmids of this invention. These plasmids are more readily detected if the vector includes a marker. Particularly useful vectors are those which contain an antibiotic-resistance marker. Plasmids of Escherichia coli, hereafter abbreviated *E. Coli*, containing such antibiotic-resistance markers are readily available. Suitable plasmids are those designated pBR322, pBR325 and pWL625. Plasmids of *Bacillus subtilis*, hereafter abbreviated *B. subtilis*, such as the plasmid pC194 which contains a gene conferring chloramphenicol resistance are also useful.

An advantage to the use of such vectors is the fact that they can exist as multiple copies within a cell. Hence, where a gene coding for alpha-amylase is introduced into these vectors, the gene is also present in multiple copies within the cells. This results in greater alpha-amylase production per cell. When strains of *E. coli* are used as the host organism, further gene amplification is possible. This is accomplished using the chloramphenicol gene amplification technique of D. B. Clewell, J. Bacteriology, 110, 667–676 (1972).

The chimeric plasmids of the present invention are constructed by first cutting naturally-occurring DNA, that contains a gene coding for a thermostable alpha-amylase enzyme, using a suitable restriction endonuclease. Donor DNA which is cut by the endonuclease is preferably plasmid DNA. This plasmid can be cut either before or after its separation from the chromosomal DNA of the donor. The endonuclease must be one which cuts the donor DNA while leaving intact the gene that codes for the alpha-amylase enzyme. A suitable endonuclease for this purpose has been found to be the enzyme Hind III.

It is also necessary to cut the vectors which are the vehicles into which the alpha-amylase coding gene is inserted. It is convenient to cut these vectors with the endonuclease used to cut the DNA of the donor microorganism. However, the vector can be cut with any endonuclease that will give linear DNA with ends that are capable of joining with ends of the fragments of donor DNA.

Cutting can be performed on a mixture of the donor DNA and the vector, or the donor DNA and the vector can be cut separately. In either case, a mixture of linear DNA sequences is obtained. Some of the linear sequences from the donor microorganism contain the alpha-amylase coding gene.

The linear DNA sequences obtained by cutting the donor DNA and the vector are mixed and ligated to form a new plasmid, the chimeric plasmid. The joining of the linear DNA sequences is accomplished by means of a ligase using techniques well known in the art. A convenient ligase for this purpose is the commercially available $T_4$ DNA ligase.

The chimeric plasmids of this invention are made biologically active by transforming them into host cells of a suitable microorganism. Suitable hosts include amylase-negative *E. coli*, strains RR1 and C600, and amylase-negative *B. subtilis*, strains ATCC No. 31,785 and Bacillus Genetic Stock Center No. 1A289. Transformation is accomplished by well-known methods. These methods include absorption of plasmids by competent cells, protoplast fusion and absorption by *E. coli* cells which have been treated with $CaCl_2$.

The cells which contain the desired plasmids are selected by screening for cells with the amylase activity of the donor. If the vector contains an antibiotic-resistance marker, preliminary screening is conveniently accomplished by plating the cells on agar plates containing the antibiotic in the medium. Only those cells containing the desired resistance will then grow. Amylase activity is determined by adding soluble starch to the plates. After growth, the plates are treated with a dilute iodine solution or exposed to iodine vapor. Only those colonies which have the desired amylase activity will show clear areas where the starch has been degraded and consequently does not stain with the iodine.

If the cells containing the recombinant plasmids produce alpha-amylase intracellularly, it is necessary to lyse the cells before the presence of the enzyme can be detected. Cells of *E. coli* are conveniently lysed with the bacteriophage $T_4$ or with D-cycloserine.

It has been found that when strains of *B. subtilis* are used as the host for the chimeric plasmids, the alpha-amylase enzyme produced by the cells is exported from the cells into the medium. This finding is important for commercial production of the enzyme, since the expensive cell lysing step is avoided. The *B. subtilis* is also a particularly desirable host because it is a species readily adapted to industrial fermentations.

Chimeric plasmids which have been produced by host cells are readily isolated by known methods One such method is the standard cleared lysate procedure of Clewell and Helinski, Biochemistry, 9, 4428–4440 (1970). They can be purified by CsCl density gradient ultracentrifugation.

The chimeric plasmids containing the alpha-amylase gene may be used as a donor for these genes. The plasmids are cut with a suitable restriction endonuclease to give linear DNA containing the alpha-amylase gene. The linear DNA may be purified by sucrose gradient ultracentrifugation. This genetic material is then combined with another vector to give a different chimeric plasmid.

The alpha-amylase produced by the host cells containing the chimeric plasmid retains its thermostable properties. This is true even if the host microorganism is a mesophile and not itself a thermophile. Furthermore, the products produced by the action of the amylase from the cloned microorganism on starch appear to be identical to those produced by the amylase of the donor microorganism.

The process of this invention can be used to transform two or more different chimeric plasmids containing genes coding for thermostable alpha-amylase into the same host microorganism. For example, E. coli RR1 was modified by the insertion of the chimeric plasmids obtained by combining a thermostable alpha-amylase gene with the vectors pBR325 and pWL625. Both plasmids were incorporated, replicated and expressed by the host cells.

The following examples illustrate certain embodiments of the present invention. Unless otherwise stated, all proportions and percentages are provided on the basis of weight.

All strains bearing ATCC numbers are available from the American Type Culture Collection, Rockville, Md.

EXAMPLE 1

Preparation of Plasmids Containing alpha-Amylase Genes and an Antibiotic-Resistance Marker Total DNA, containing genes for alpha-amylase was isolated from cells of a strain of B. stearothermophilus, ATCC No. 31,783, by the general method of Berns and Thomas, J. Molec. Biol., 11, 476–490 (1965). In the present process, the cells were suspended in a mixture of 50 mM tris(hydroxymethyl)aminomethane hydrochloride (hereafter written Tris-HCl) at pH 8, 0.6 mM ethylenediaminetetraacetic acid (hereafter written EDTA) and 25% sucrose instead of in Standard Saline Citrate. They were also treated with lysozyme (2 mg/ml) for 1 hour at 0° C. prior to lysis. Plasmid pBR322 DNA, the restriction enzyme Hind III, and $T_4$ DNA ligase were obtained from the Bethesda Research Laboratories, Bethesda, Md.

A mixture of 7.5 μg total DNA from B. stearothermophilus, 7 units (U) of restriction enzyme Hind III, and 10 μg of Bovine Serum Albumin in a 100 μl solution which contained 50 mM NaCl, 6 mM Tris-HCl at pH 7.5 and 6 mM $MgCl_2$, was incubated at 37° C. for 30 minutes. 2.2 μg of plasmid pBR322 DNA and 7 U of Hind III were digested in 20 μl of a similar solution for 1 hour at 37° C. Analysis of the DNA on agarose gel showed that the digestion was complete. Then 6.75 μg of the digested B. stearothermophilus DNA and 1.8 μg of the digested pBR322 DNA were mixed in 0.3 ml of a solution containing 66 mM Tris-HCl (pH 7.6), 6.6 mM $MgCl_2$, 10 mM dithiothreitol and 0.067 mM adenosine triphosphate (hereafter written ATP) and joined using 0.28 units of $T_4$ DNA ligase. Analysis on agarose gels of the DNA after ligation showed that the ligation was complete with no detectable linear pBR322 DNA remaining.

EXAMPLE 2

Transformation of Plasmids Containing alpha-Amylase Genes and an Antibiotic-Resistance Marker into E. coli A culture of E. coli RR1, available as strain PRC 399 from the Plasmid Reference Center, Stanford University Medical Center, Stanford, Calif., was grown on the following medium:

|  | g/Liter |
| --- | --- |
| Tryptone | 10.0 |
| Yeast Extract | 5.0 |
| Sodium Chloride | 5.0 |
| Glucose | 1.0 |

The culture was grown in a tube overnight at 37° C. It was then diluted with 9 parts of the same medium and incubated at 37° C. for an additional 135 minutes with vigorous agitation. The cells were harvested by centrifugation and washed with cold 0.1 M NaCl solution. The harvested E. coli cells were prepared for transformation by the calcium chloride method of Cohen, et al, Proc. Nat. Acad. Sci., U.S.A., 9. 2110–2114 (1972).

One-half of the ligated DNA prepared in Example 1 was transformed into the cells of E. coli RR1. The cells were cultivated on plates containing the same medium on which the E. coli cells were grown except that the medium contained ampicillin at a concentration of 50 μg/ml. By this means, only cells of E. coli containing the plasmid pBR322 (with ampicillin-resistant genes) were obtained.

As a means of determining the number of cells containing recombinant DNA, the ampiqillin-resistant cells were checked for resistance to tetracycline. Since insertion of a piece of DNA in the Hind III cut site of pBR322 usually inactivates the plasmid gene for tetradycline resistance, the frequency of tetracycline sensitivity gives the number of recombinant DNA-containing cells present in the population of cells. Transformation yielded $3.6 \times 10^4$ ampicillin-resistant cells per milliliter and $3.0 \times 10^4$ tetracycline-resistant cells per milliliter. Therefore, about 16% of the cells were sensitive to tetracycline, showing they have plasmids containing recombinant DNA.

EXAMPLE 3

Isolation of alpha-Amylase-Producing Colonies of E. coli

A medium was prepared with the same composition as that used for the growth of E. coli except that 15 g/liter of agar plus ampicillin (50 μg/ml) was added. This medium was placed in 130 petri plates and inoculated with diluted transformed E. coli prepared as in Example 2. These plates yielded an average of 113 colonies per plate. The colonies were allowed to grow until they were about 1–2 mm in diameter before they were replica plated onto a starch medium of the following composition:

|  | g/Liter |
| --- | --- |
| $Na_2HPO_4$ | 6 |
| $KH_2PO_4$ | 3 |
| NaCl | 0.5 |
| $NH_4Cl$ | 1 |
| Yeast Extract | 1 |
| Peptone | 10 |
| Agar | 15 |
| Lintner's Starch | 10 |

After 3 hours of growth, bacteriophage $T_4$, available as ATCC No. 11303-B4, is added to the plates in an overlay containing starch. About $1 \times 10^7 T_4$ are used per plate to lyse the growing E. coli thus liberating any intracellular enzymes. After an overnight growth and lysis, a 2.5% solution of Lugol's iodine solution was poured on the plates to detect any clear zones produced by amylase activity Of the approximately 15,000 colonies present, 18 colonies produced clear zones indicating the presence of amylase. The colonies containing amylase activity were replica plated and again shown to contain amylase activity. However, the amylase activity was only exhibited after the addition of T4 for cell lysis indicating that the amylase was produced intracellularly. Further experimentation indicated that D-cycloserine was as efficient as T4 for lysing the cells when the drug was added to the overlay medium at a concentration of 600 µg/ml.

A strain of *E. coli* RR1 containing the plasmid vector pBR322 with an amylase gene is available as ATCC No. 31,789.

EXAMPLE 4

Transformation of Plasmids Containing alpha-Amylase Genes and an Antibiotic-Resistance Marker into a Second Strain of *E. coli*

A culture of *E. coli* C600, ATCC No. 23,724, was grown and the cells were harvested and prepared for transformation according to the procedure of Example 2.

Five different amylase clones obtained in Example 3 were grown and the recombinant plasmids were extracted by the standard cleared lysate procedure of Clewell and Helinski, Biochemistry, 9, 4428-4440 (1970). The partially purified plasmid DNA was suspended in a mixture of 10 mM Tris-HCl and 1.0 mM EDTA at pH 7.5 prior to transformation into the CaCl$_2$ treated *E. coli* cells. This DNA was analyzed and shown to be sterile, so that no amylase-producing colonies would be due to expression of cells introduced with the DNA. The transformed cells were grown on medium containing ampicillin to allow only cells containing plasmids to grow. When the colonies were checked for amylase activity, there was 100% correlation between presence of plasmids and amylase activity. Thus, plasmid DNA clearly is shown to transform both strains of *E. coli* to give amylase producers, showing that the phenomenon is not strain dependent, but that it does require the recombinant plasmid.

A strain of *E. coli* C600 containing the plasmid vector pBR322 with an amylase gene is available as ATCC No. 31,788.

EXAMPLE 5

Thermostability of the alpha-Amylase

Four amylase clones obtained in Example 3 and one control *E. coli* RR1 culture were grown in 15-ml cultures using the culture medium of Example 2. The cells were lysed by addition of D-cycloserine before the cell debris was removed by centrifugation Sodium acetate and calcium chloride were added to the supernatant fluids to give a concentration of 50 mM and 2.5 mM, respectively, and the pH was adjusted to 6.0. The enzyme solutions were placed in screw-capped test tubes lined with Teflon tape. The solutions were assayed for amylase activity before and after heating to 90° C. for 45 minutes. Amylase activity was determined by the rate of starch hydrolysis as reflected in the rate of decrease in iodine-staining capacity, measured spectrophotometrically, according to the general procedure of B. W. Smith and J. H. Rowe, J. Biol. Chem., 179, 53 (1949). The control *E. coli* showed no amylase activity. Purified amylases from *B. stearothermophilus*, ATCC No. 31,783, *B. subtilis* available from the Sigma Chemical Co., St. Louis, Mo., as Sigma A6380[1]), and Termamyl, a thermostable alpha-amylase available from Novo Laboratories, Inc., Wilton, Conn., were added to the control *E. coli* lysate to serve as standards for thermostability. The results of the analyses are shown in Table 1.

[1]) Although the Sigma Chemical Company catalog lists this enzyme as an alpha-amylase from *B. subtilis*, H. Chung and F. Friedberg, Biochem. J., 185, 387-395 (1980) have shown that it is from *Bacillus amyloliquefaciens*.

TABLE I

THERMOSTABILITY DATA

| Source of Cell Lysate | Initial Activity, U/ml | Activity After 45 min., 90° C., U/ml | % Activity Remaining |
|---|---|---|---|
| *E. coli* RR1 (Control) | 0 | 0 | — |
| Control + *B. stearothermophilus* α-amylase (from ATCC 31,783) | 0.21 | 0.15 | 71.4 |
| Control + Termamyl | 0.39 | 0.34 | 87.2 |
| Control + *B. subtilis* α-amylase (Sigma A6380) | 0.21 | 0.01 | 4.8 |
| Control + Clone 1 | 0.45 | 0.38 | 84.4 |
| Control + Clone 2 | 0.22 | 0.18 | 81.8 |
| Control + Clone 3 | 0.36 | 0.29 | 81.0 |
| Control + Clone 4 | 0.42 | 0.35 | 83.3 |

The amylase produced by the clones is seen to be at least as heat stable as the enzyme produced by the donor *B. stearothermophilus*. It is comparable in heat stability to the commercial thermostable alpha-amylase, Termamyl, and is clearly superior in heat stability to the alpha-amylase from a commercial *B. subtilis*.

Hydrolyzates obtained by digesting starch with each of the amylases were analyzed by thin layer chromatography to identify the low molecular weight sugars produced. The relative amounts of low molecular weight sugars formed by the amylases from the *E. coli* clones were similar to the amounts of sugars formed by known alpha-amylases used as controls.

These results show that the gene for a heat-stable enzyme obtained from an extreme thermophile has been faithfully expressed in a mesophilic bacterial host to yield a heat-stable enzyme product. It has thus been discovered that a gene from a highly thermophilic bacterium may be expressed in a mesophilic bacterium using recombinant DNA methods. Furthermore, the synthesis of the active thermostable enzyme occurs at normal mesophilic temperatures (approximately 20°-40° C.).

EXAMPLE 6

Isolation of Naturally Occurring Plasmids Containing alpha-Amylase Genes

Total DNA was isolated from the cells of *B. stearothermophilus*, ATCC No. 31,783, by the procedure given in Example 1. Plasmid DNA was separated from the total DNA by CsCl ethidium bromide ultracentrifugation by the method of R. Radloff, W. Bauer and J. Vinograd, Proc. Natl. Acad. Sci., U.S.A., 57, 1514-1521 (1967). This plasmid DNA was shown to contain an alpha-amylase gene by the following procedure:

Plasmid DNA was cut using the restriction enzyme Hind III as in Example 1. Clones were formed by introducing this DNA into *E. coli* as in Examples 1-3. Analysis of the tetracycline-resistant phenotype showed that 3.3% of the cells were tetracycline sensitive and therefore contained cloned DNA. Screening for cells with alpha-amylase activity showed that 0.42% or about 1 of every 8 cells containing cloned DNA had the amylase gene. Cutting of the *B. stearothermophilus* plasmids with Hind III yields linear pieces of DNA which separate into 8 readily detectable bands upon electrophoresis on agarose gel. The frequency of cloning the amylase piece ($\frac{1}{8}$) is about as expected if one of the 8 predominant bands had the amylase gene. Furthermore, analysis of these plasmid bands shows that one of the bands is about 3.6 Md, the same size as the cloned piece of DNA which was obtained from analysis of the plasmids of Example 1.

This experiment clearly indicates that at least one alpha-amylase gene is located on a naturally-occurring plasmid in the strain of *B. stearothermophilus* employed.

EXAMPLE 7

Preparation and Isolation of Strains of *E. coli* Containing Different Chimeric Plasmids A. A culture of the amylase-producing *E. coli* isolated in Example 3, ATCC No. 31,789, was grown overnight in the medium used in Example 2. The plasmid DNA was amplified according to the procedure of Clewell, D. B., J. Bacteriology, 110, 667–676 (1972), using 170 μg of chloramphenicol per ml. The following medium was used for amplification:

|  | g/Liter |
|---|---|
| $Na_2HPO_4$ | 6.0 |
| $KH_2PO_4$ | 3.0 |
| NaCl | 0.5 |
| $NH_4Cl$ | 1.0 |
| Casein Amino Acids | 5.0 |
| Glucose | 2.0 |
| $CaCl_2.2H_2O$ | 0.015 |
| $MgSO_4.7H_2O$ | 0.246 |
| Vitamin $B_1$ | 0.001 |

Plasmid DNA was then isolated by the standard cleared lysate method of Clewell and Helinski, Biochemistry 9, 4428–4440 (1970). The isolated plasmids were purified by the CsCl, ethidium bromide method of Example 6 and then by extraction with isopropanol and extensive dialysis into 10 mM Tris plus 1 mM EDTA at pH 7.5.

A culture of *E. coli* RR1, PRC 399, containing the 3.9 Md plasmid pBR325, was grown and the plasmid DNA was amplified, isolated and purified by the procedures of the preceding paragraphs.

Plasmid DNA from the two sources was cut with restriction enzyme Hind III. Solutions of the cut plasmids were mixed and ligated at 0° for 18 hours by the general procedure of Example 1.

The ligated DNA was transformed into *E. coli* RR1 by the method described in Example 2. The cells were diluted and plated on agar plates containing chloramphenicol at a concentration of 25 μg/ml. By this means, only cells of *E. coli* containing the plasmid pBR325 (with chloramphenicol-resistant genes) were obtained. Colonies of cells which appeared were screened for amylase activity by the method described in Example 3 using D-cycloserine to lyse the cells.

The recombinant plasmid DNA from three colonies that showed amylase activity and were resistant to chloramphenicol was extracted by the cleared lysate procedure as in Example 4. Separation of the recombinant plasmids on agarose gels showed that they were the proper size for a combination of plasmid pBR325 plus a 3.6 Md fragment containing the amylase gene. Digestion of the plasmid with Hind III enzyme gave a 3.6 Md fragment and the linear form of pBR325. This example shows that the amylase gene can be recloned on a different vector, pBR325, without loss of its amylase-producing activity. The resulting *E. coli* strain is available as ATCC No. 31,792.

B. The chloramphenicol and ampicillin resistant chimeric plasmid produced in Part A was used as the donor of the DNA fragment which contains the alpha-amylase gene. This fragment was combined with the 10 Md vector plasmid pWL625 using the general procedure of Part A. Plasmid pWL625 is described by W. Goebel, et al, Molec. Gen. Genet., 157, 119–129 (1977). It can be isolated from a culture of a strain of *E. coli*, ATCC No. 31,787, by the plasmid isolation method used in Part A of this example. This vector confers resistance to the antibiotics, ampicillin and kanamycin. Insertion of DNA into pWL625 at the Hind III site destroys kanamycin resistance.

Cells of *E. coli* RR1, which had been transformed with the recombinant DNA, were grown on agar plates containing ampicillin. Those colonies resistant to ampicillin, not resistant to chloramphenicol due to pBR325, and showing amylase activity, were selected for analysis. Plasmid DNA was isolated from the colonies. Analysis on agarose gels before and after digestion with Hind III enzyme showed that the fragment of DNA containing the amylase gene was cloned on the pWL625 plasmid to yield a new plasmid. The strain of *E. coli* containing this chimeric plasmid is available as ATCC No. 31,791.

EXAMPLE 8

Transformation of Two Different Chimeric Plasmids into One Strain of *E. coli*

The amylase-producing *E. coli* strain prepared in Example 7B was grown and prepared for transformation by the procedure of Example 2. The purified plasmid prepared in Example 7A was transformed into these cells. When the resulting cells were grown on agar plates containing chloramphenicol, all of the colonies showed amylase activity. Plasmid DNA was isolated from one of the colonies and analyzed on agarose gels. The chimeric plasmids described in Example 7A and Example 7B were both found to be present. This experiment demonstrates that *E. coli* can grow and maintain simultaneously two different chimeric plasmids containing alpha-amylase genes. The long-term stability of this combination of plasmids has not been determined. The strain of *E. coli* containing these two chimeric plasmids is available as ATCC No. 31,790.

EXAMPLE 9

Transformation of Plasmids Containing alpha-Amylase Genes and an Antibiotic-Resistance Marker into a Strain of *B. subtilis*

A. Donor DNA Preparation: The chimeric plasmid produced in Example 7B was used as the donor of the DNA fragment which contains the alpha-amylase gene. It was extracted by the cleared lysate procedure of Clewell and Helsinki, Biochemistry, 9, 4428–40 (1970). This plasmid DNA was cut with restriction enzyme Hind III. The digest was mixed with a small amount of ethidium bromide and separated using the sucrose gradient method of El-Gewely and Helling, Anal. Biochem., 102, 423–428 (1980). The 3.6 Md fragment containing the alpha-amylase gene was extracted twice with n-butyl alcohol, precipitated with an equal volume of isopropyl alcohol and suspended in 10 mM Tris plus 1 mM EDTA at pH 7.5 and kept at −20° C. until used.

B. Vector Preparation: A strain of *B. subtilis*, available from the Bacillus Genetic Stock Center, Dept. of Microbiology, Ohio State University, Columbus, Ohio, as Strain No. 1E17, containing the 2.0 Md plasmid pC194, which contains a gene conferring chloramphenicol resistance, was streaked onto a plate containing tryptic soy agar available from the Difco Laboratories, Detroit, Michigan (hereafter abbreviated Difco) and 50 μg/ml of chloramphenicol. Cells were then inoculated into 150 ml of Penassay broth (Difco) in a 1-liter flask and the cells were grown overnight at 37° C. with shaking. The cells were pelleted and resuspended into 10 ml protoplasting buffer (25% sucrose, 0.1 M NaCl-0.05 M Tris-HCl at pH 7.5 and 0.05 M EDTA at pH 8.13). Five mg of egg white lyzozyme (Sigma Chemical Company) was added for 30 minutes at 37° C. Next 13 ml of 2% sodium dodecyl sulfate in 0.7 M NaCl was gently mixed, followed by 2.4 ml 5 M NaCl. The mixture was chilled in ice water and centrifuged at 12,100×g for 20 minutes.

The DNA was precipitated with an equal volume of isopropyl alcohol. The solid was held in ice water for 60 hours before it was collected by centrifugation and suspended in a solution containing 0.01 M Tris hydrochloride and 0.001 M EDTA at pH 7.5. Plasmid DNA was separated by CsCl ethidium bromide ultracentrifugation by the method of Radloff, et al, Proc. Natl. Acad. Sci., U.S.A., 57, 1514–1521 (1967). The 2 Md plasmid was treated by extraction with isopropyl alcohol and extensive dialysis into 10 mM Tris plus 1 mM EDTA at pH 7.5.

C. Chimeric Plasmid Preparation: The 2 Md vector from Part B was cut with Hind III restriction enzyme and mixed with the 3.6 Md DNA fragment from Part A. Concentrations of the vector and donor DNA's were 6 μg/ml and 17 μg/ml, respectively. Ligation was accomplished by the general procedure of Example 1. The absence of any linear 3.6 Md fragment after ligation as shown by agarose gel electrophoresis, indicated that ligation was complete. D. Transformation of the Chimeric Plasmid into *B. subtilis:* A culture of *B. subtilis*, ATCC No. 31,785, which does not contain an amylase gene, was grown overnight on a plate containing Tryptose Blood Agar Base (Difco) and 1% soluble starch. To the plate was added 2 ml of the following growth medium:

|  | Percent |
| --- | --- |
| (NH4)2SO4 | 0.2 |
| K2HPO4 | 1.4 |
| KH2PO4 | 0.6 |
| Sodium Citrate.2H2O | 0.1 |
| MgSO4.7H2O | 0.12 |
| Glucose | 0.5 |
| Casamino Acids (Difco) | 0.02 |
| L-Tryptophan | 0.005 |

About 0.1 ml of the cell suspension so obtained was added to 10 ml of the same medium in a 250-ml flask and incubated at 37° C. with vigorous agitation for 4 hours. Then 1 ml of the culture was added to 9 ml of pre-warmed transformation medium at 37° C., and incubation with shaking was continued for 90 minutes. The transformation medium was the same as the growth medium except that it contained 0.01% casamino acids, and 0.0005% L-tryptophan. To 0.25 ml of cells containing about $1 \times 10^8$ cells/ml was added 5 μl of the chimeric plasmid solution from Part C containing 0.12 μg of the plasmid. The mixture was shaken gently at 37° C. for 30 minutes. The mixture was diluted with an equal volume of Penassay broth (Difco) and shaking at 37° C. was continued for an additional 90 minutes. Cells, 0.1 ml aliquots, were spread on plates containing Tryptose Blood Agar Base (Difco), 1% soluble starch and 20 μg/ml chloramphenicol. As controls, *B. subtilis* cells with no added plasmid and *B. subtilis* cells with the vector plasmid pC194 were plated on the same medium.

No colonies were seen on the plates where the cells contained no added plasmid. Three colonies were seen on the plates where the cells contained the plasmid pC194, but none of these colonies showed amylase activity.

One colony was observed on the plates plated with cells containing the chimeric plasmid DNA of Part C. This gave a clear zone on exposure to iodine vapor indicating that extracellular amylase enzyme was produced by these cells. The cells appear to require the presence of chloramphenicol for stability. This culture is available as ATCC No. 31,786.

A sample of the DNA from the amylase containing colony was separated by agarose gel electrophoresis. A plasmid band of about 5.6 Md was observed. This corresponds to the size of the chimeric plasmid of Part C.

The purified chimeric plasmid was cut with Hind III restriction enzyme and subjected to agarose gel electrophoresis. Two fragments of about 2.0 Md and 3.6 Md were obtained. These correspond to the sizes of the donor DNA of Part A and the vector DNA of Part B.

E. Transformation of the Chimeric Plasmid into a Second Strain of *B. subtilis:* The chimeric plasmid containing the amylase gene was isolated from the cells of the amylase producing colony of Part D by the procedure used for isolation of the pC194 plasmid in Part B. The isolated chimeric plasmid was transformed into another amylase negative strain of *B. subtilis*, strain No. 1A289, available from the Bacillus Genetic Stock Center, Dept. of Microbiology, Ohio State University, Columbus, Ohio. Transformation was accomplished by the protoplast fusion method of S. Chang and S. N. Cohen, Molec. Gen. Genet., 168, 111–115 (1979). When the cells were grown on plates as in Part D, about $1 \times 10^8$ colonies/ml were seen on plates containing no chloramphenicol. About $1 \times 10^3$ colonies/ml were seen on plates containing chloramphenicol. All of these colonies showed the presence of amylase by the starch-iodine test. This amylase containing *B. subtilis* is available as ATCC No. 31,784.

EXAMPLE 10

Thermal Stability of the alpha-Amylase Produced by the *B. subtilis* Containing the Chimeric Plasmid The *B. subtilis* containing the chimeric plasmid of Example 9E, ATCC No. 31,784, was grown in 1 liter of medium in a 2.8-liter Fernbach flask using the following medium:

|  | Percent |
| --- | --- |
| Corn Starch | 9.0 |
| Corn Steep Liquor | 6.0 |
| Yeast Autolysate[a] | 0.35 |
| (NH4)2HPO4 | 1.0 |
| KH2PO4 | 0.1 |

| | Percent |
|---|---|
| CaCl$_2$.2H$_2$O | 0.06 |
| MnCl$_2$.4H$_2$O | 0.05 |
| Corn Oil | 1.0 |
| Termamyl | (0.05 U/ml) |

*a*Prymex 154 available from Amber Laboratories, Juneau, Wisconsin.

The medium was autoclaved for 30 minutes at 121° C., which destroys Termamyl activity, and subsequently cooled to room temperature. Then 0.01 mg of chloramphenicol per ml was added to the medium before inoculation with the cells. The broth was centrifuged and the thermostability test was performed on a diluted sample of the supernatant liquid using the general procedure of Example 5. For comparison, the thermostability of amylases from B. stearothermophilus, B. subtilis, as well as commercial Termamyl in incubation medium containing 50 mM sodium acetate and 2.5 mM CaCl$_2$ was also measured. (These were the same comparison amylases used in Example 5.) The results of the tests are shown in Table II.

TABLE II

THERMOSTABILITY DATA

| Enzyme Sample | Initial Activity, U/ml | Activity After 45. min., 90° C., U/ml | % Activity Remaining |
|---|---|---|---|
| B. stearothermophilus | 1.81 | 1.16 | 64 |
| B. subtilis | 1.34 | 0 | 0 |
| Termamyl | 1.26 | 0.79 | 63 |
| Enzyme from ATCC No. 31,784 | 1.58 | 1.07 | 68 |

In this test, the amylase produced by the B. subtilis clone, ATCC No. 31,784, is seen to be at least as heat stable as the enzyme produced by the donor B. stearothermophilus. It is comparable in heat stability to the commercial thermostable alpha-amylase, Termamyl, and is clearly superior in heat stability to the alpha-amylase from B. subtilis.

Thus, it is apparent that there has been provided, in accordance with the invention, a process for the preparation of chimeric plasmids containing a gene coding for a thermostable alpha-amylase enzyme and for their use to prepare a thermostable alpha-amylase that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for constructing a chimeric plasmid having a gene coding for a thermostable alpha-amylase which comprises:
   (a) cutting naturally-occurring plasmid DNA present in a strain of B. stearothermophilus having a gene coding for a thermostable alpha-amylase to obtain a linear DNA sequence containing the alpha-amylase coding gene;
   (b) cutting a suitable vector to obtain a second linear DNA sequence; and
   (c) joining the linear DNA sequences of Steps (a) and (b).

2. The process of claim 1 wherein the vector is a plasmid selected from the group consisting of E. coli plasmids pBR322, pBR325 and pWL625; and B. subtilis plasmid pC194.

3. The process of claim 1 wherein the strain of B. stearothermophilus is selected from the group consisting of B. stearothermophilus, ATCC Nos. 31,195; 31,196; 31,197; 31,198; 31,199; and 31,783.

4. The process of claim 1 wherein the cutting is accomplished by means of a restriction endonuclease.

5. The process of claim 4 wherein the endonuclease is the enzyme Hind III.

6. The process of claim 1 wherein the linear DNA sequences are joined by means of a ligase.

7. The process of claim 6 wherein the ligase is T$_4$ DNA ligase.

8. A process for constructing a chimeric plasmid having a gene coding for a thermostable alpha-amylase which comprises:
   (a) cutting a chimeric plasmid, prepared by the method of claim 1, to obtain a linear DNA sequence containing the alpha-amylase coding gene;
   (b) cutting a suitable vector to obtain a second linear DNA sequence; and
   (c) joining the linear DNA sequences of Steps (a) and (b).

9. The process of claim 8 wherein the vector is a plasmid selected from the group consisting of E. coli plasmids pBR322, pBR325 and pWL625; and B. subtilis plasmid pC194.

10. The process of claim 8 wherein the strain of B. stearothermophilus is selected from the group consisting of B. stearothermophilus, ATCC Nos. 31,195; 31,196; 31,197; 31,198; 31,199; and 31,783.

11. The process of claim 8 wherein the cutting is accomplished by means of a restriction endonuclease.

12. The process of claim 11 wherein the endonuclease is the enzyme Hind III.

13. The process of claim 8 wherein the linear DNA sequences are joined by means of a ligase.

14. The process of claim 13 wherein the ligase is T$_4$ DNA ligase.

15. A chimeric plasmid having a gene coding for a thermostable alpha-amylase having the same thermostable characteristics as those of the alpha-amylase produced by B. stearothermophilus ATCC #31,783, which plasmid comprises a DNA sequence containing the alpha-amylase gene cut from naturally-occurring plasmid DNA present in a strain of B. stearothermophilus and the DNA of a suitable vector.

16. The chimeric plasmid of claim 15 wherein the strain of B. stearothermophilus is selected from the group consisting of B. stearothermophilus, ATCC Nos. 31,195; 31,196; 31,197; 31,198; 31,199; and 31,783.

17. The chimeric plasmid of claim 15 wherein the vector is a plasmid selected from the group consisting of E. coli plasmids pBR322, pBR325 and pWL625; and B. subtilis plasmid pC194.

18. A microorganism comprising at least one chimeric plasmid of claim 15.

19. The microorganism of claim 18 wherein the microorganism is a bacterium.

20. The microorganism of claim 19 wherein the bacterium is E. coli.

21. The microorganism of claim 19 wherein the bacterium is B. subtilis.

22. A process for preparing a thermostable alpha-amylase which comprises the steps of:
   (a) introducing at least one chimeric plasmid of claim 15 into a host microorganism;
   (b) culturing the microorganism containing the chimeric plasmid in a suitable medium; and
   (c) isolating the alpha-amylase produced by the cultured microorganism.

* * * * *